United States Patent
Miller

Patent Number: 6,058,936
Date of Patent: May 9, 2000

[54] MEDICAL/ATHLETIC WRAP

[76] Inventor: John Nick Miller, P.O. Box 560247, Charlotte, N.C. 28256

[21] Appl. No.: 09/094,950

[22] Filed: Jun. 15, 1998

Related U.S. Application Data

[62] Division of application No. 08/619,839, Mar. 19, 1996.

[51] Int. Cl.[7] ..................................... A61B 19/00
[52] U.S. Cl. ................................ 128/869; 602/60; 602/75
[58] Field of Search ..................................... 128/869, 882; 602/8, 20, 21, 60, 61, 62, 63, 75

[56] References Cited

U.S. PATENT DOCUMENTS

| | | | |
|---|---|---|---|
| 2,711,168 | 6/1955 | Brickman | 602/8 |
| 2,935,065 | 5/1960 | Homier | 602/8 |
| 4,131,114 | 12/1978 | Kirkpatrick | 602/8 |
| 5,439,439 | 8/1995 | Green | 602/8 |

*Primary Examiner*—Michael A. Brown
*Attorney, Agent, or Firm*—Kennedy Covington Lobdell & Hickman, L.L.P.

[57] ABSTRACT

A roll of sheet material is disclosed for use in medical and/or athletic wrapping of a body part. The roll includes a hollow, cylindrical, core with a sheet of plastic film wound thereupon. The axial dimensions of the core and film are limited so that the core and the film can be supported in an open hand between the thumb and the middle and ring fingers, and between the index finger and the little finger. The method of wrapping the body part includes wrapping the film from the core around the body part by moving the roll from a first location to a second location with one hand, transferring the roll from that hand to the second hand such that the second hand engages the roll between the thumb and the middle finger at opposite axial ends, continuing wrapping the body part by moving the second hand with the roll partially around the body part back to the first location, at which point the roll is transferred to the first hand. The roll is held in the first hand such that the roll is supported between the thumb and the middle and ring fingers, and with the index finger and the little finger engaging opposite axial ends of the core.

8 Claims, 6 Drawing Sheets

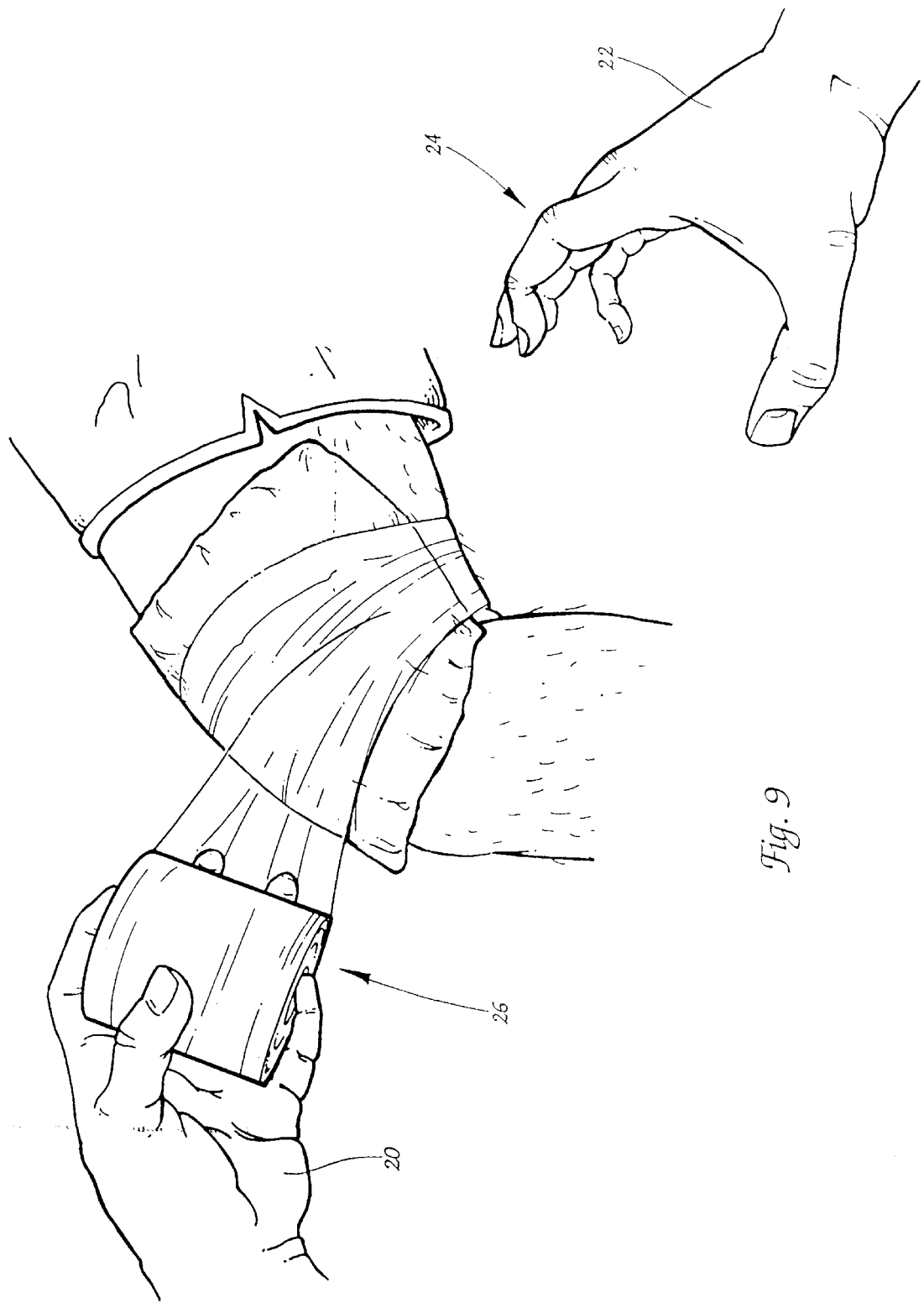

MEDICAL/ATHLETIC WRAP

This application is a divisional of Ser. No. 08/619839, filed Mar. 19, 1996, now abandoned.

BACKGROUND OF THE INVENTION

The present invention relates to application of a plastic film around an item and, more specifically, relates to a method for medical and/or athletic wrapping of a body part with a plastic stretch film.

Often, it is desirable to wrap a body part of an individual with a plastic stretch film. Such wrapping can be, for example, to secure an ice pack to a wounded area, to strengthen and/or immobilize a joint, or to wrap the laces of the shoes of an athletic participant to ensure that loose shoe laces do not hinder the performance of the athlete.

One such device that is used to dispense such film is disclosed in Parry et al U.S. Pat. No. 4,722,493 and Parry et al U.S. Pat. No. 4,872,623. This device inserts a special handle into a roll of film, the interior of said handle rotating with the roll of film. By exerting a gripping pressure on the exterior of the handle, friction is applied to the rotating interior of the handle which then is used to adjust the rate of dispensing of the film from the roll.

Other patents also have been issued for devices that provide braking novelties to control the speed of the roll as the wrap is being applied to the item. These devices also generally have an additional handle or other such item insertable into the core of the roll to enable one to grip a handle while still allowing for the rotation of the core and the roll while applying the wrap to an item. Some such devices are provided that are inserted into both sides of a roll to enable two hands to control the film as it is being wrapped around, for example, a very large item. Examples of these devices are found in Parry U.S. Pat. No. 4,179,081; Parry U.S. Pat. No. 4,530,473; Parry et al U.S. Pat. No. 5,203,517; Parry U.S. Pat. No. 4,248,392; and Strout et al U.S. Pat. No. 4,522,348.

These devices may work well when wrapping large items or items for shipment in commerce. However, there exists a need for such a device to apply plastic film in a medical or athletic wrapping application. Such prior art devices are unwieldy and cumbersome when such plastic film is to be wrapped around a body part, for example, to secure an ice pack to an injured area, or to wrap the shoelaces of an athlete's shoe. With such a device, there is a certain amount of stressful and deleterious torque placed on the wrist of the user, the handle assembly adds unnecessary weight to the device, twisting and binding is encountered when wrapping the body part, the tension of the film and the speed at which the film is wrapped is only indirectly controlled by pressure on the handle, when transferring the device between hands, one hand is necessarily in the location that the other hand must grasp—thus interfering with the transfer, and such device can be cumbersome and unwieldy when trying to wrap a body part.

Thus, it would be desirable to provide a roll of sheet material for use in medical and athletic wrapping of human body parts that may be easily maneuvered by one hand of an attendant to encircle the body part for which the wrapping is desired without needing or using any special or additional devices. It is further desirable to provide such a roll with sufficiently limited dimensions that it would easily fit into a hand and may be transferred from hand to hand as the wrapping of the body part occurs.

SUMMARY OF THE INVENTION

It is an object of the present invention to provide a roll of sheet material for use in medical and athletic wrapping of body parts that is easily maneuverable with a single hand of an attendant. It is further an object of the present invention to provide a roll of sheet material with sufficiently limited dimensions such that it may be placed in one hand and transferred from one hand to another hand easily as the wrapping of the body part occurs. It is a further object of the present invention to provide a method of wrapping wherein the roll of sheet material is maneuvered with one hand during the wrapping of a body part and transferred from one hand to another hand to accomplish complete wrapping thereof. It is a further object that the speed and tension with which the film is dispensed from the roll is controlled directly by pressure from the fingers and the hand upon the roll of material.

The present invention provides a method of medical or athletic wrapping of a body part from a wound roll of plastic film. The roll comprises a cylindrical core and a sheet of plastic film wound on the core. The core and the film have an axial extent that is limited so that the core and the film can be supported in an open hand between the index finger and the little finger of the hand, and a radial extent limited so that the roll can be grasped between the thumb and middle and ring fingers of the hand. The index finger and the little finger engage opposite axial ends, and the thumb and the middle and ring fingers grasp substantially opposite radial extents, of the core and the film in order to provide support, guidance, and tension to the core and the film to control the speed and tension with which the film is wrapped around the body part.

The method comprises holding such a roll in a first hand, unwinding an end segment of film from the roll with a second hand, and wrapping the end segment and the roll around the body part in opposite directions. Then, the end segment is tucked against the body part and under the film that has been disengaged from the roll, the roll is transferred from the first hand to the second hand, at which time the roll is taken in the second hand between the thumb and middle finger, the thumb and middle finger being placed at opposite axial ends of the roll. The cylindrical core of the roll may be hollow and, if so, the thumb and the middle finger may be placed comfortably within the hollow of the core. Then, the body part is wrapped with the film by moving the second hand with the roll partially around the body part from a first position to a second position, at which point the roll is moved from the second hand back into the first hand. When the roll is taken in the first hand, it is held such that the roll is supported by the hand with the index finger and the little finger being placed at and engaging opposite axial ends of the roll. This minimizes undesired axial movement of the roll and provides for the ability to squeeze the roll to control the tension and speed with which the film is unwrapped. If the cylindrical core is hollow, the index finger and little finger may be slightly placed within the hollow of the core. The diameter of the roll is sufficiently limited so that the roll can be grasped between the thumb and the middle and the ring fingers. This allows these fingers and the associated muscle structure to control the tension and speed with which the film is unwrapped.

Then, the first hand with the roll is moved from the second position to the first position to continue to wrap the film further around the body part. Then the roll is moved from the first hand into the second hand and the above steps are repeated as desired to encircle the body part as many times as necessary. Then, the film that is wrapped around the body part is severed from the film wound upon the roll, and the loose end of the film wrapped around the body part is secured to eliminate the tendency of the wrapped film to unwrap. The movement of the first hand and the second hand is in the same revolutional direction in order to completely encircle the body part to be wrapped as many times as is desired.

The core of the roll preferably has a longitudinal dimension that is not greater than the longitudinal dimension of the plastic film wound about the core. The core may be hollow and generally has an outer diameter of between about one inch and about two inches, an inner diameter of about one inch, and a longitudinal dimension of between about two and one-half inches and about three and one-half inches. Such dimensions allow for nimble, easy, and effective maneuvering of the roll between the hands and around the body part to be wrapped, resulting in an efficient and effective wrap of the body part.

BRIEF DESCRIPTION OF THE DRAWINGS

FIGS. 8 and 9 are views of the method of wrapping another body part in accordance with the present invention and also illustrate the dimensions with respect to a hand and the grip recited in the present invention.

DESCRIPTION OF THE PREFERRED EMBODIMENT

Figure 1:
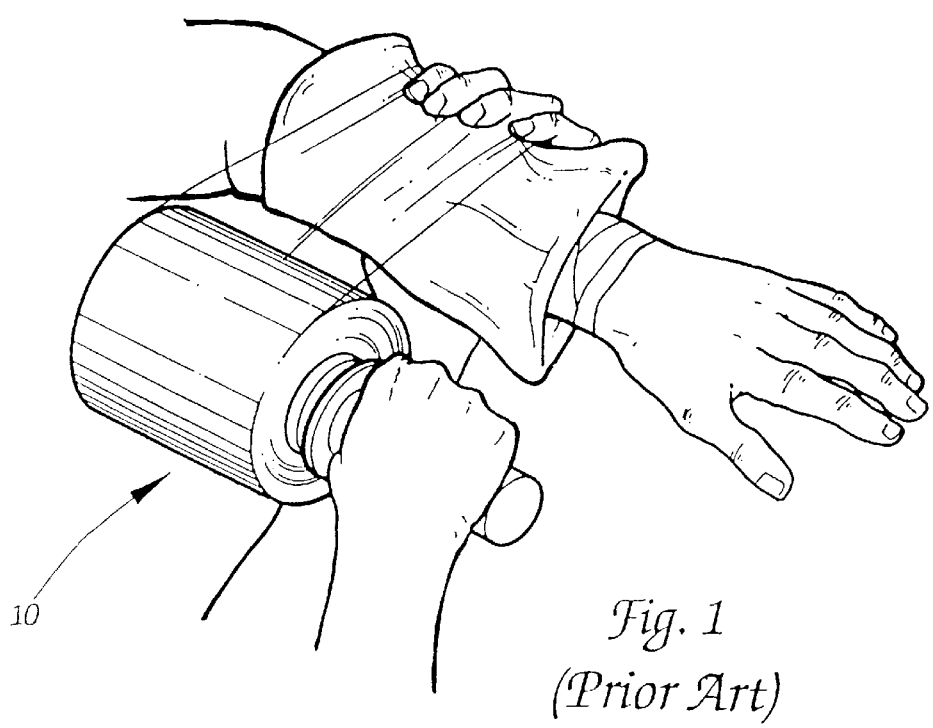
FIG. 1 is a perspective view of a prior art device in use while wrapping a body part.
Figure 2:
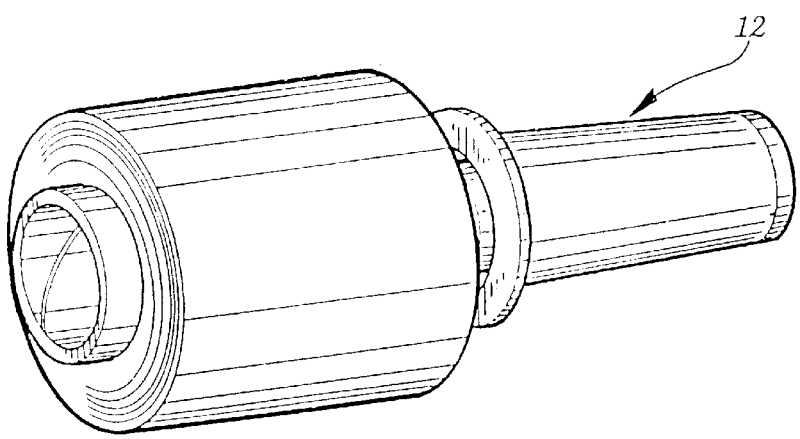
FIG. 2 is a perspective view of the prior art device of FIG. 1.

Devices for use in medical and athletic wrapping of body parts are generally of designs similar to that illustrated in FIGS. 1 and 2. Using such a device, plastic film is wrapped around a body part by revolutional movement of the roll 10 with a handle 12 around the body part, transferring the handle 12 from one hand to the other, and continuing the revolutional motion of the handle 12 and the roll 10 around the body part. While such device may be suitable for wrapping objects for packaging, it has drawbacks, as previously discussed, when being used to wrap a body part.

Figure 3:
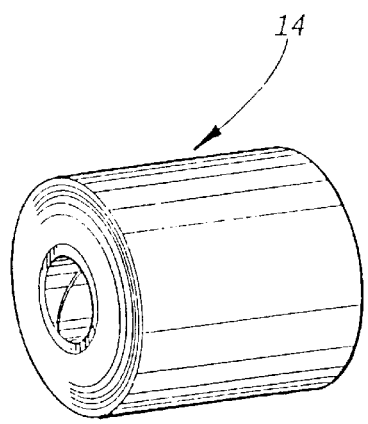
FIG. 3 is a perspective view of the roll used in the method of the present invention.

The roll 14 used in the preferred method of the present invention, illustrated in FIG. 3, is comprised of a cylindrical core 16 and a sheet of plastic film 18 wound on the core. Advantageously, no external and peripheral attachments are necessary for the present invention to accomplish its objectives.

Figure 4:
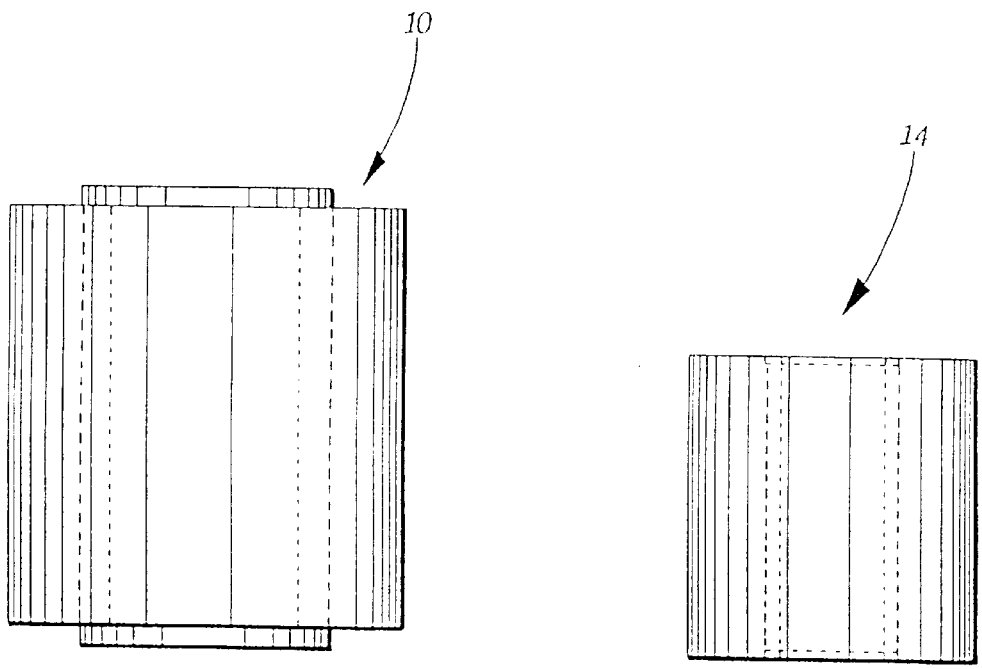
FIG. 4 is top elevational view of the unsuitably large roll of the prior art device and the roll used in the method of the present invention.
Figure 5:
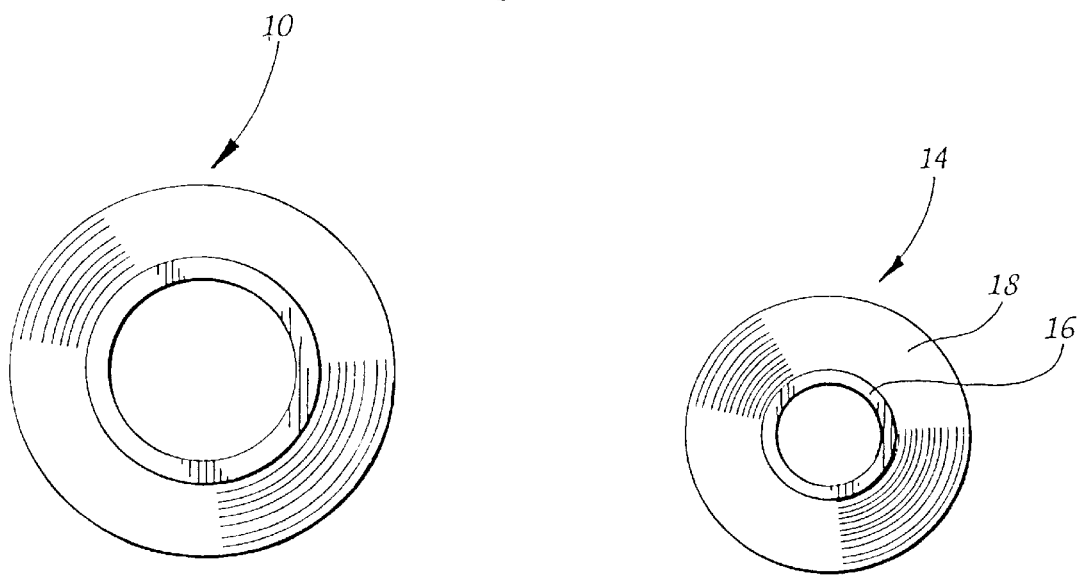
FIG. 5 is an end view of a the unsuitably large roll of the prior art device and the roll used in the method of the present invention.

The dimensions of the core 16 are sufficiently limited such that the core 16 and the film 18 can be supported in an open hand between the index finger and the little finger, and between the thumb and the middle and ring fingers. The index finger and the little finger engage opposite axial ends of the core 16 and the film 18, and provide support to the roll 14 when the roll 14 is in other than a perfectly horizontal position. This also allows for the little finger and the index finger, in combination with other muscles in the hand, to exert a force upon the roll 14 to control the tension of the film 18 as it is unwrapped from the core 16 and to control the speed of rotation and revolution of the roll 14 as it is used to wrap a body part. The thumb and the middle and ring fingers are placed at substantially opposite radial extents so that these fingers and thumb can grasp the roll 14 to provide tension and speed control to the roll 14. Generally, the longitudinal (axial) dimension is less than about five inches and preferably between about two and one-half inches and about three and one-half inches. The diameter is preferably limited to about that which occurs when 500 feet of 90 gauge plastic stretch film 18 is wound on the core 16. FIGS. 4 and 5 illustrate the dimensions of the roll 14 of the present invention compared to a conventional roll 10 for use in prior art devices and prior art methods.

Preferably, the core 16 is cylindrical and hollow, with an inner diameter of about one inch. This allows for various fingers to be inserted into the hollowed core during different stages of wrapping of the body part to further control the direction, tension, and speed of the film 18 as it is unwrapped from the core 16 and onto the body part. Such construction also utilizes less material and is therefore cheaper and less heavy to manufacture and ship. The hollow, cylindrical core 16 is also preferably constructed of reinforced cardboard to further reduce the costs and the weight associated with its construction. The axial dimension of the core 16 is not greater than the axial dimension of the film 18 that is wound around the core 16. This provides an additional slight indentation between the core 16 and the film 18 that may be used to assist control of the direction, tension, and speed with which the film 18 is wrapped around the body part.

The core 16 has an outer diameter of between about one inch and about two inches. Such outer diameter must be sufficiently dimensioned such that a beneficial amount of film 18 may be wound around the core 16 without exceeding an overall diameter of the roll 14 that would result in the roll 14 not being handleable between the thumb and the middle and ring fingers and being cumbersome and unwieldy in wrapping a body part. As previously indicated, a preferable diameter is that which results from 500 feet of 90 gauge plastic stretch film 18 being wound upon the core 16.

A sheet of plastic stretch film 18 is wound around the core 16 such that the film 18 may be unwound from the core 16 as the core 16 and film 18 are moved around a body part. Suitable material for the plastic stretch film includes plasticized polyvinyl chloride, low density polyethylene, and ethylene vinyl acetate. However, it is to be noted that any type of film may be wound around the core 16 without departing from the spirit of the invention. The plastic stretch film 18 may be used to secure another item, such as an ice pack or a hot pack (see FIGS. 8 and 9), to the body part, or may be used to wrap a body part, such as a knee or an ankle, to help support the body part and to minimize injury thereto during an athletic endeavor. The plastic film 18 may also be applied to potential loose ends to minimize interference with the athletic endeavor. For example, the plastic stretch film 18 may be wrapped around a shoe to ensure that the loose ends of shoe laces do not interfere with the athlete as he or she participates in activities (see FIGS. 6 and 7).

Such plastic film 18 may also be used to secure electrodes to body parts, such as for monitoring bodily electroactivity or for medical iontophoresis treatment. It is also to be noted that use of this invention is not limited to application of a plastic film around human body parts, but also may extend to wrapping animal body parts, such as is encountered in thoroughbred horse racing situations or other veterinary applications.

The plastic stretch film 18 is wound evenly around the core 16 so that the film 18 is easily unwound from the core 16 in an orderly fashion when the core 16 and the film 18 are moved around a body part to wrap the body part with the film 18. Generally, the width of the film 18 (its axial dimension) is at least equal to the axial dimension of the core 16. The axial dimension of the core 16 is not greater than the axial dimension of the plastic film 18 wound about the core 16. This provides a slight indentation at the core 16 so that the fingers may more easily guide, support, and control the roll 14 and its movement as it wraps the body part.

By sufficiently limiting the dimensions of the roll 14 to enable easy handling with a single hand, the roll 14 of the present invention is uniquely situated for application in medical and athletic wrapping of body parts. This wrapping may be conducted quickly and with a minimum of problems encountered by using devices of the prior art, as discussed above.

Figure 6:
FIGS. 6 and 7 are views of the method of wrapping a body part in accordance with the present invention illustrating the dimensions with respect to a hand and the grip recited in the present invention.
Figure 7:
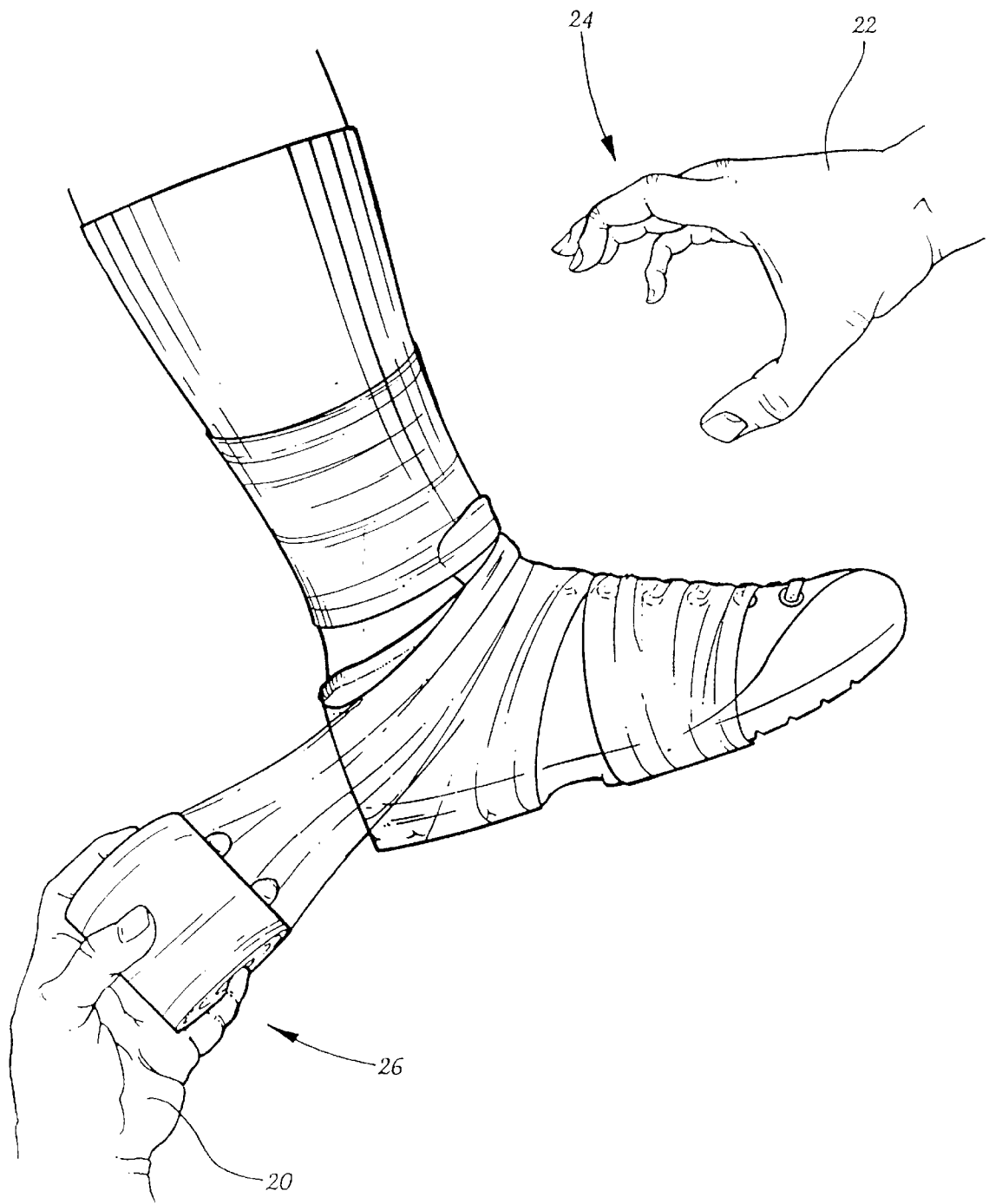
Figure 8:
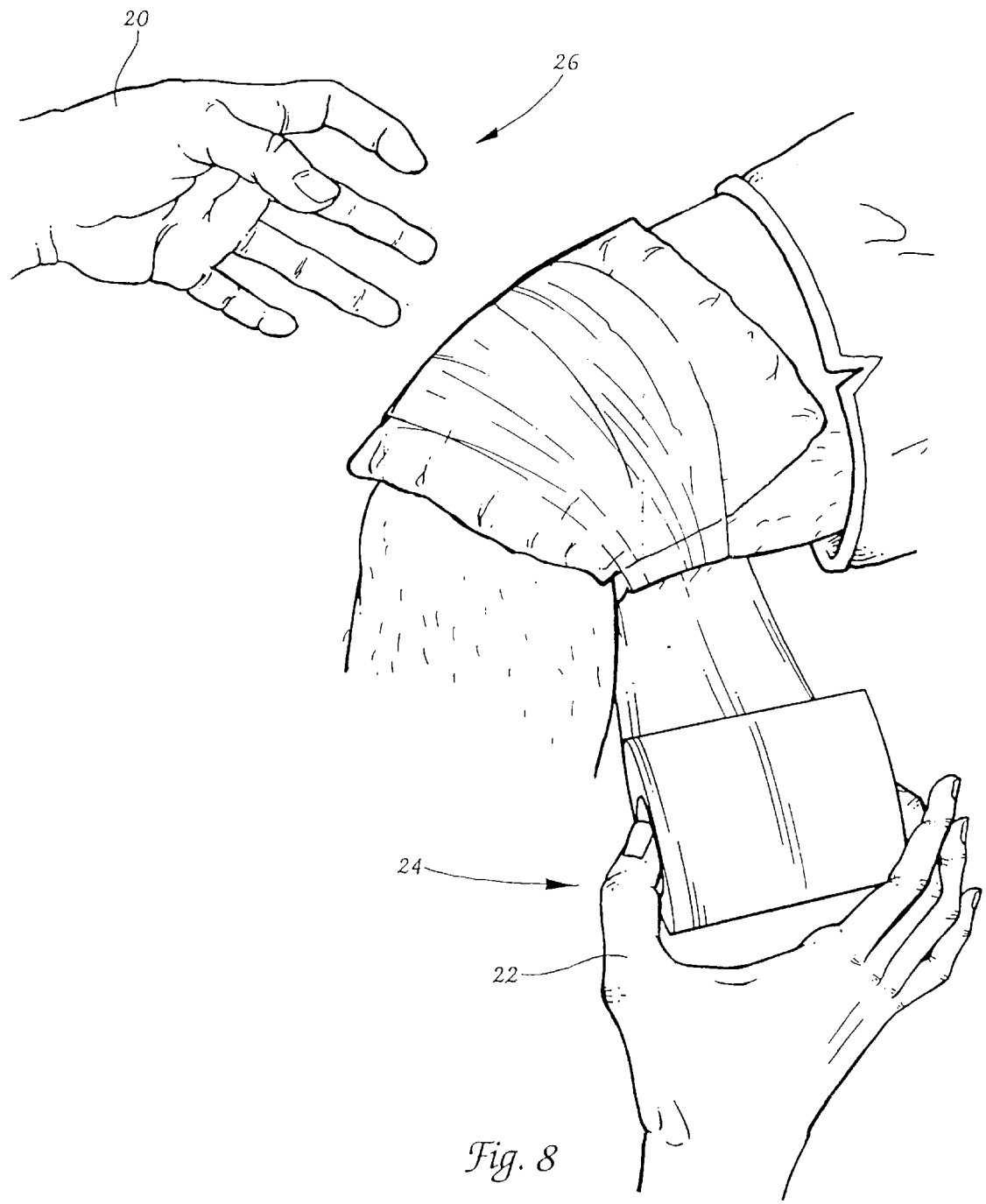

The method of the present invention of medical or athletic wrapping of a body part from a wound roll 14 of plastic stretch film 18 is illustrated in FIGS. 6 and 7, in which an ankle is wrapped, and in FIGS. 8 and 9, in which a knee is wrapped, and is described as follows. The roll 14 is held in a first hand 20 and the a second hand 22 disengages a loose end of film 18 from the roll 14. The hands 20,22 are then moved apart, resulting in a section of the film 18 being unwound from the roll 14. Then the end segment (not shown) of this film 18 and the roll 14 are wrapped around the body part in opposite directions. This encircles the body part with the end segment of the film 18 and the roll 14 containing the remainder of the film 18. This is necessary in order to commence wrapping the body part.

The end segment is then tucked against or nearly against the body part to be wrapped and under a section of the film 18 that has been unwound from, but is still attached to, the roll 14. The roll 14 is then transferred from the first hand 20 to the second hand 22 while maintaining the location of the end segment between the body part to be wrapped and the film 18 that has been unwound from, but is still attached to, the roll 14.

When the transfer to the second hand 22 occurs, the roll 14 is taken between the thumb and the middle finger of the second hand 22; the thumb and middle finger are placed at opposite axial ends of the roll 14. Preferably, the thumb and middle finger are slightly inserted into a hollow or indentation provided in the end of the core 16 resulting from the core 16 being of lesser axial extent than the wound plastic film 18. This enables the roll 14 to freely rotate as it revolves around the body part to be wrapped. Held in this manner, the roll is moved with the second hand 22 partially around the body part from a first position 24 in relation to the body part to a second position 26 in relation to the body part. It is not necessary that these positions 24,26 be 180° apart, so long as there is a first position 24 and a second position 26 with relation to the body part. When the second hand 22 with the roll 14 arrives at the second position 26, the roll 14 is then transferred from the second hand 22 into the first hand 20.

The roll 14 is held in the first hand 20 such that the roll 14 is supported by the hand with the index finger and little finger being placed at opposite axial ends of the roll and graspable between the thumb and the middle and ring fingers at substantially opposite radial extents. This transfer is made possible because the location of the thumb and the middle finger of the second hand 22 is such that there is no interference with the index finger and little finger of the first hand 20 engaging the opposite axial ends of the roll 14. This allows for a quick and efficient transfer of the roll 14 from one hand 20,22 to the other hand 22,20, quite unlike the cumbersome prior art mechanism, as illustrated in FIGS. 1 and 2. In the prior art, each hand has to grasp the handle in the same place, so that a transfer from one hand to another by necessity must result in one hand interfering with the other.

By placing the index finger and little finger at opposite axial ends of the roll 14, these fingers may be used, in combination with the thumb and the middle and ring fingers, to control, direct, and moderate the speed and direction of the roll 14 as it is wrapping the body part. For example, if the wrapping occurs such that the axial dimension of the core 16 is disposed at an angle other than perfectly horizontal, the roll 14 would have a tendency to slide off the supporting hand, if not retained and supported by a finger. This placement of the fingers also allows for pressure to be placed by the little finger and/or index finger on the roll 14 while it is revolved around the body part in order to control the tension and the speed with which the film 18 is unwound from the roll 14 and wrapped around the body part. The index finger and the little finger preferably engage opposite axial ends of the roll 14, and are slightly inserted into a hollow or indentation provided at each axial end.

Then the wrapping is continued around the body part by moving the first hand 20 with the roll 14 from the second position 26 to the first position 24 in the same revolutional direction as the movement from the first position 24 to the second position 26. Movement in this direction ensures that the body part is encircled by the motions of hands 20,22 and the transferring of the roll 14. The above movement of hands 20,22, with the roll 14 and the transferring between hands 20,22 of the roll 14 is continued until the desired amount of film 18 is wrapped around the body part. It is to be noted that first position 24 and second position 26 may not be in identical physical locations during each wrapping cycle and need not be 180° apart. The exact spacing of positions 24,26 is not critical, as the wrapping continues to completely wrap the body part. These positions 24,26 are simply defined as points of reference for each individual wrapping cycle.

After the desired amount of film 18 is wrapped around the body part, the film 18 is severed from the unwound film 18 on the roll 14. The loose end of film 18 wrapped around the body part is then secured so that the loose end does not begin to unwrap that film 18 wrapped around the body part.

The film 18 that is wound upon the core may be of any color and may be selected to match, for example, the team colors if the film 18 is to be used in a team athletic application. The film 18 may also be clear so that when it is wrapped around a shoe or other device or article of clothing, the logos or designs on the shoe or other article of clothing will be visible. Likewise, the construction material of the film 18 or the core 16 may be varied to suit the demands of the application without departing from the spirit of the invention.

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A method of medical/athletic wrapping of a body part from a wound roll of plastic stretch film comprising the steps of:

(a) holding the roll in a first hand such that the roll is supported by the first hand with the index finger and the little finger being placed at and engaging opposite axial ends of the roll;

(b) wrapping the body part with the film by moving the first hand with the roll partially around the body part from a first position to a second position relative to the body part;

(c) transferring the roll at the second position to a second hand by taking the roll in the second hand between the thumb and the middle finger, the thumb and the middle finger being placed at and engaging opposite axial ends of the roll;

(d) wrapping the body part with the film by moving the second hand with the roll partially around the body part from the second position to the first position;

(e) transferring the roll at the first position to the first hand by taking the roll in the first hand between the index finger and the little finger, the index finger and the little finger being placed at and engaging opposite axial ends of the roll;

(f) repeating steps (b) through (e) to complete the wrapping; and then (g) severing the film wrapped around the body part from the film wound on the roll and securing the film wrapped around the body part.

2. The method of claim 1, wherein said holding of the roll in the first hand includes grasping the diameter of the roll between the thumb and the middle finger and the ring finger.

3. A method of medical/athletic wrapping of a body part from a wound roll of plastic stretch film comprising the steps of:

(a) providing a wound roll of plastic stretch film;

(b) holding the roll in a first hand;

(c) unwinding an end segment of film from the roll with a second hand;

(d) wrapping the end segment and the roll around the body part in opposite directions;

(e) tucking the end segment against the body part;

(f) transferring the roll from the first hand to the second hand;

(g) taking the roll in the second hand between the thumb and the middle finger, the thumb and the middle finger being placed at opposite axial ends of the roll;

(h) wrapping the body part with the film by moving the second hand with the roll partially around the body part from a first position in relation to the body part to a second position in relation to the body part;

(i) transferring the roll from the second hand into the first hand;

(j) holding the roll in the first hand such that the roll is supported by the first hand with the index finger and the little finger being placed at and engaging opposite axial ends of said roll, thus minimizing undesired axial movement of the roll;

(k) wrapping the body part further by moving the first hand with the roll from the second position to the first position around the body part;

(l) transferring the roll from the first hand into the second hand;

(m) repeating steps (g) through (l) to complete the wrapping; and then (n) severing the film wrapped around the body part from the film wound on the roll and securing the film wrapped around the body part.

4. The method of claim 3, wherein the step of providing the wound roll includes providing a wound roll comprising a hollow, cardboard, cylindrical core having a film wound therearound and having an inner diameter of about one inch, an outer diameter of between about one inch and about two inches, and an axial dimension between about two and one-half and about three and one-half inches.

5. The method of claim 1, wherein the step of providing the wound roll includes providing a wound roll comprising a hollow cylindrical core and plastic film wound thereupon, the axial dimension of the core being not greater than the axial dimension of the film.

6. A method for making an athletic/medical wrapping of a body part by wrapping plastic stretch film around the body part from a roll of the plastic stretch film having axial ends thereof alternately supported by and held in direct contact with a first hand and a second hand.

7. The method of claim 6, wherein a first of the axial ends of the roll of plastic stretch film is supported by the thumb of the first hand and a second of the axial ends is supported by at least one finger of the first hand.

8. The method of claim 6, wherein the axial ends of the roll of plastic stretch film are spaced apart an axial distance of between about two and one-half and three and one-half inches.

* * * * *